(12) United States Patent
Rice et al.

(10) Patent No.: US 9,718,294 B2
(45) Date of Patent: Aug. 1, 2017

(54) DEVELOPMENT OF LATENT FRICTION RIDGE PRINTS

(71) Applicant: CONSOLITE FORENSICS LIMITED, Salisbury Wiltshire (GB)

(72) Inventors: Nicholas Rice, Wincanton Somerset (GB); John Bond, Leicester Leicestershire (GB); Kevin Byrne, Zeals Wiltshire (GB); James Price, Salisbury Wiltshire (GB); Christopher King, Sherbourne Dorset (GB); Richard Lewis, Shaftesbury Dorset (GB)

(73) Assignee: Consolite Forensics Limited, Salsibury (GB)

( * ) Notice: Subject to any disclaimer, the term of this patent is extended or adjusted under 35 U.S.C. 154(b) by 0 days.

(21) Appl. No.: 14/401,976

(22) PCT Filed: Dec. 21, 2012

(86) PCT No.: PCT/GB2012/053252
§ 371 (c)(1),
(2) Date: Nov. 18, 2014

(87) PCT Pub. No.: WO2013/186511
PCT Pub. Date: Dec. 19, 2013

(65) Prior Publication Data
US 2015/0133295 A1    May 14, 2015

(30) Foreign Application Priority Data

Jun. 11, 2012 (GB) .................................. 1210206.7

(51) Int. Cl.
*B41M 1/14* (2006.01)
*B41M 3/00* (2006.01)
(Continued)

(52) U.S. Cl.
CPC ............. *B41M 3/14* (2013.01); *A61B 5/1172* (2013.01); *B41M 3/001* (2013.01); *B41M 3/142* (2013.01); *B41M 5/30* (2013.01); *G06K 9/00006* (2013.01)

(58) Field of Classification Search
CPC .......... B41M 3/00; B41M 3/001; B41M 1/14; B41M 1/142; A61B 5/117; A61B 5/1172;
(Continued)

(56) References Cited

U.S. PATENT DOCUMENTS 5,601,867 A     2/1997  Riedl
6,885,439 B2 *  4/2005  Fujieda ............... G06K 9/0004
                                               356/71

(Continued)

FOREIGN PATENT DOCUMENTS

CN      1176692 A        3/1998
DE      19724252    * 12/1998  ............ G01N 21/78
WO      2005067608 A2    7/2005

OTHER PUBLICATIONS

International Search Report and Written Opinion mailed May 3, 2013 (PCT/GB2012/053252); ISA/EP.
(Continued)

*Primary Examiner* — Bruce H Hess
(74) *Attorney, Agent, or Firm* — Banner & Witcoff, Ltd.

(57) ABSTRACT

Apparatus to produce a spatially and temporally uniform heat source is described and this is used to visualize latent fingerprints deposited onto thermal paper by raising the temperature of the paper. Results show an improvement over previous techniques, particularly when fingerprint deposits are aged or the developed fingerprints faint; visualization being enhanced by the use of an LED light source. An investigation of the components in fingerprint sweat likely to affect the solubility and hence colour change of the dye present in the thermal paper has shown that polar protic
(Continued)

Figure 1A:
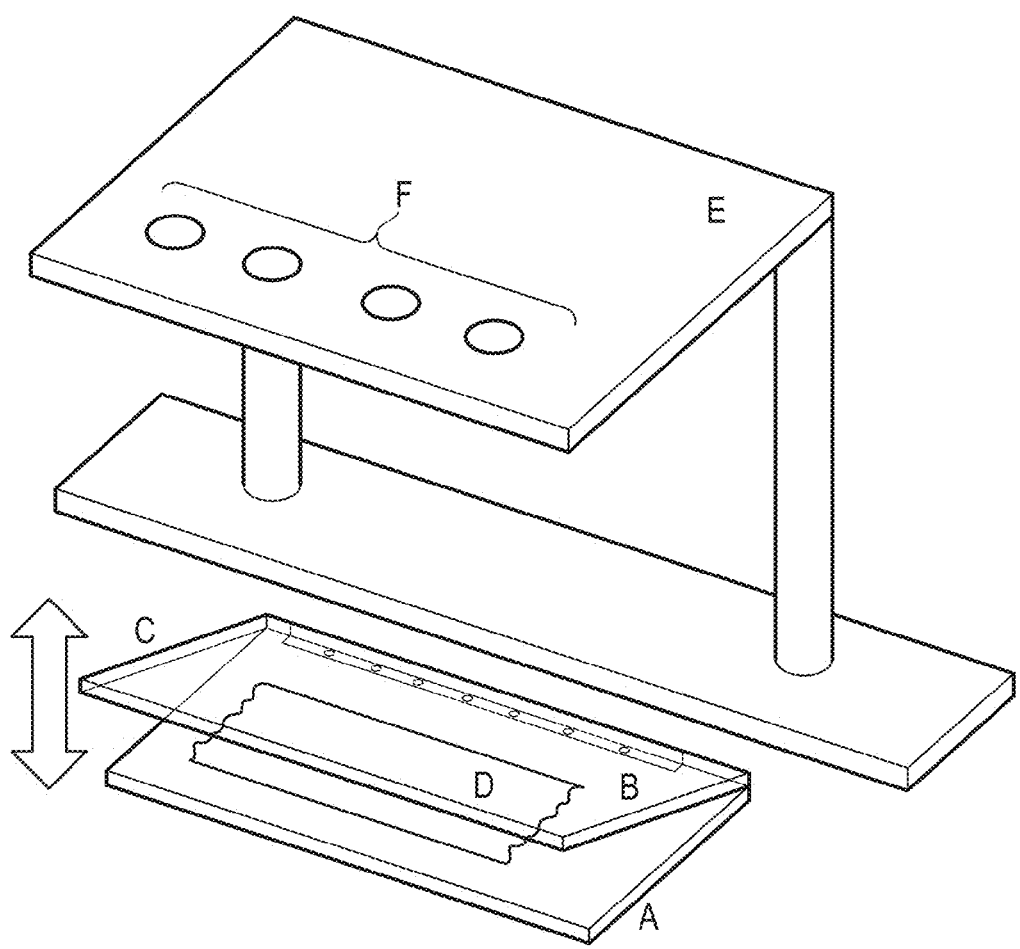

solvents able to donate a proton are favoured and a polar amino acid found commonly in eccrine fingerprint sweat (lysine) has been shown able to produce the desired colour change. Aged fingerprint deposits on thermal paper from a variety of sources up to four years old have been visualized with this technique.

5 Claims, 11 Drawing Sheets

(51) Int. Cl.
    *A61B 5/117*     (2016.01)
    *G06K 9/00*     (2006.01)
    *B41M 3/14*     (2006.01)
    *B41M 5/30*     (2006.01)
    *A61B 5/1172*     (2016.01)

(58) Field of Classification Search
    CPC .... G01N 21/64; G01N 21/6456; G01N 21/71; G06K 9/00; G06K 9/00006
    USPC .............................................. 503/201; 427/1
    See application file for complete search history.

(56) References Cited

U.S. PATENT DOCUMENTS

2007/0026130 A1    2/2007    Arndt
2011/0076383 A1    3/2011    Reedy et al.

OTHER PUBLICATIONS

UKIPO Search Report mailed Jun. 18, 2013 (GB1210206.7).
Foster + Freeman You Tube, May 22, 2012 (May 22, 2012). XP002695041, Retrieved from the Internet: URL:http://www.youtube.com/watch?v=fETEdN19pUE [retrieved on Apr. 9, 2013] the whole document.
Foster + Freeman: "Using the TFD-2 to develop latent fingerprints on paper" Sep. 2011 (Sep. 2011) XP002695042 Retrieved from the Internet: URL:http://www.fosterfreeman.co.uk/index.php?option=com_phocadownload&view=file&id=725:tfd-2&Itemid=186 [retrieved on Apr. 9, 2013] the whole document.
Consolite, "Hot print system" http://www.consolite.co.uk/Forensics/downloads/HPS%20Datasheet.pdf See whole document.
Mindich, David, http://ezinearticles.com/? The-Uses-and-Hazards-of-Thermal-Paper&id=4141727, Submitted on Apr. 20, 2010.
Bowman V, editor. Manual of Fingerprint Development Techniques. 2nd rev. ed. Sandridge, UK: Police Scientific Development Branch, Home Office, pp. 85-93, dated 2004.
Manual of Use for ThermaNin, http://www.bvda.com/EN/prdctinf/en_thermanin.html, dated Jan. 26, 2011.
Broniek B, Knaap W. Latent Fingerprint Development on Thermal Paper Using Muriatic (Hydrochloric) Acid, J Forensic Ident, 52:427-32, dated 2002.
Schwarz L, Frerichs I., Advanced Solvent-Free Application of Ninhydrin for Detection of Latent Fingerprints on Thermal Paper and Other Surfaces, J Forensic Sci, 47:1274-7, dated 2002.
Sears V. Latent Fingerprint Development on Thermal Paper Using Muriatic (Hydrochloric) Acid. J Forensic Ident, 52:678, dated 2002.
Ma R. , Wei, Qun, Chemical fuming: A Practical Method for Fingerprint Development on Thermal Paper. J Forensic Ident, 56:364-73, dated 2006.
Takatsu M, Kageyama H, Hirata K, Akashi S, Yoko Ta T et al. Development of a New Method to Detect Latent Fingerprints on Thermal Paper With O-alkyl Derivative of Ninhydrin, Rep Nat Res Inst Police Sci, 44:1-6, dated 1991.
Schwarz L, Klenke I. Enhancement of Ninhydrin or DFO Treated Latent Fingerprints on Thermal Paper, J Forensic Sci; 52:649-55, dated 2007.
Schwarz L, Klenke I. , Improvement in Latent Fingerprint Detection on Thermal Paper Using a One-Step Ninhydrin Treatment with Polyvinylpyrrolidones (PVP), J Forensic Sci; 55: 1076-9, dated 2010.
The Weekly Detail . . . The internet newsletter for Latent Print Examiners, http://www.clpex.com/ Articles/TheDetail/I-99/TheDetail97.htm, dated Jun. 16, 2003.
Wakefield M, Armitage S., The Development of Latent Fingerprints on Thermal Paper Using a Novel, Solvent-Free Method, J Forensic Ident; 55:202-13, dated 2005.
Scott M., Improved Results in the Development of Latent Fingerprints on Thermal Paper, J Forensic Ident; 58 (4):424-8, dated 2008.
Migron Y., Hocherman G., Springer E., Almog J., Mandler D. Visualization of Sebaceous Fingerprints on Fired Cartridge Cases: A Laboratory Study, J Forensic Sci; 43:543-548, dated 1998.
Worley CG, Wiltshire SS, Miller TC, Havrilla GJ, Majidi V., Detection of Visible and Latent Fingerprints Using Micro-X-Ray Fluorescence Elemental Imaging, J Forensic Sci;51 :57-63, dated Jan. 2006.
Ramotowski RS. Composition of Latent Finger Print Residue, In: Lee HC, Gaensslen RE, editors. Advances in Fingerprint Technology, New York: Elsevier; 63-104, dated 2001.
Bandey H.L., Fingerprint Development and Imaging Newsletter: The Powders Process, Study 1. Sandridge: Police Scientific Development Branch, Home Office; Report No. 54/04, dated 2004.
Clayden J., Greeves N., Warrens, Wothers P., Organic Chemistry, Oxford: Oxford University Press; Introducing Kinetics: How to Make Reactions Go Faster and Cleaner, pp. 255-256, dated 2001.
May 24, 2016—(CN) Office Action—U.S. Appl. No. 14/401,976—Eng Tran.

\* cited by examiner (a) (b)

DEVELOPMENT OF LATENT FRICTION RIDGE PRINTS

The present application is a U.S. National Phase filing of International Application No. PCT/GB2012/053252, filed Dec. 21, 2012, designating the United States of America and claiming priority to United Kingdom Patent Application No. 1210206.7 filed Jun. 11, 2012, and the present application claims priority to and the benefit of all the above-identified applications, which are all incorporated by reference herein in their entireties.

The present invention relates generally to the field of fingerprinting and particularly to the visualisation of latent friction ridge skin prints.

Although the word latent means hidden or invisible, in modern usage and particularly for forensic science the term "latent prints" means any chance or accidental impression left by friction ridge skin on a surface, regardless of whether it is visible or invisible at the time of deposition.

The basis of the traditional fingerprinting technique is simple. Skin on the surface of the hands and feet forms ridges, so-called papillary ridges or friction ridges, in patterns that are unique to each individual and which do not change over time. Friction ridge skin present on the soles of the feet and toes (plantar surfaces) is as unique in its ridge detail as are the fingers and palms (palmar surfaces). Even identical twins (who share their DNA) do not have identical fingerprints.

The friction ridges are raised portions of the epidermis on the digits (fingers and toes), the palm of the hand or the sole of the foot, consisting of one or more connected ridge units of friction ridge skin. These are sometimes known as "epidermal ridges" which are caused by the underlying interface between the dermal papillae of the dermis and the interpapillary pegs of the epidermis. These ridges serve to amplify vibrations triggered, for example, when fingertips brush across an uneven surface, better transmitting the signals to sensory nerves involved in fine texture perception. They also assist in gripping rough surfaces and improve surface contact in wet conditions.

The skin has deposits of oil and perspiration that normally coat the surface. When the hand or foot touches the surface, some of the moisture is transferred to the object, leaving an impression of the friction ridge detail. These are referred to as latent impressions. The impressions consist usually of a substantial proportion of water with small traces of amino acids and chlorides mixed with a fatty, sebaceous component which contains a number of fatty acids and triglycerides.

On most surfaces the latent impressions are not readily visible. The best way to render latent prints visible, so that they can be photographed or otherwise processed, can be complex and depends, for example, on the type of surfaces on which they have been left.

The present invention is concerned particularly with prints which have been deposited onto thermal paper.

Thermal paper is a special fine paper which is coated with a chemical that changes colour when exposed to heat. It is used, for example, in thermal printers and particularly in inexpensive or lightweight devices such as adding machines, cash registers, and credit card terminals. The surface of the paper is coated with a solid-state mixture of a dye and a suitable matrix; for example a combination of a fluoran leuco dye and octadecylphosphonic acid. When the matrix is heated above its melting point, the dye reacts with the acid, shifts to its coloured form, and the changed form is then conserved in a metastable state when the matrix solidifies back quickly enough. Usually such coatings will turn black when heated, but coatings that turn blue or red are sometimes used.

In recent years, the use of thermal paper for rapid and low noise printing of receipts has become more widespread (1). This extended use has prompted the investigation of suitable ways of enhancing latent fingerprint deposits on thermal paper, as polar organic solvents such as those used in conventional treatments for latent fingerprint enhancement on paper (2) initiate colouring of the leuco dye in thermal paper, thus making fingerprint visualization problematic (3). A number of chemical treatment methods have been reported to overcome this problem (4-8) with, most recently, integrating polyvinylpyrrolidones into a ninhydrin solution to prevent the colour change of the leuco dye (9,10). In addition to these chemical treatments, the application of heat has been reported to develop latent fingerprints on thermal paper (11). Wakefield and Armitage (12) assessed the effectiveness of a low temperature application of heat using a commercially available hair dryer held 5 cm above the paper surface and found that latent fingerprints developed at a temperature approximately 30° C. less than the normal colour change temperature of the paper. A slight variation in development temperature was attributed to the dye/acid combination in different brands of thermal paper. Wakefield and Armitage found that latent fingerprint ridge detail could be developed on thermal paper by the application of heat up to two weeks after fingerprint deposition, depending on the brand of thermal paper. Subsequently, Scott (13) increased the humidity by placing a beaker of water on a hot plate underneath the paper being treated by the application of heat and found that latent fingerprints developed as black on white images.

The present invention includes apparatus constructed to provide a more controlled method of heating thermal papers to the temperature required to develop latent fingerprints and then show how the use of a light source (for example built into the apparatus) can enhance visualization of aged and faintly developed fingerprint deposits. Results are compared to the findings of Wakefield and Armitage and an assessment is made of the effectiveness of the apparatus on both fresh and aged (up to four weeks) fingerprint deposits on thermal paper. Reasons why fingerprint sweat affects thermal paper in this way are investigated. The effectiveness of the apparatus to develop latent fingerprints on aged thermal paper receipts from a variety of sources (automatic teller machines, supermarket checkouts, credit/debit card transactions and supermarket product labels) is demonstrated.

According to an aspect of the present invention there is provided apparatus for visualising latent friction ridge prints deposited onto thermal paper, the apparatus comprising a spatially and temporally uniform heat source for raising the temperature of a thermal paper sample.

A further aspect provides a thermal paper print visualisation apparatus for developing latent friction ridge prints deposited onto thermal paper, the apparatus comprising a spatially and temporally uniform heat source for raising the temperature of a thermal paper sample.

A further aspect provides a thermal paper print recovery apparatus for developing latent friction ridge prints deposited onto thermal paper, the apparatus comprising a spatially and temporally uniform heat source for raising the temperature of a thermal paper sample.

A further aspect provides apparatus for developing latent friction ridge prints deposited onto thermal paper, the apparatus comprising a spatially and temporally uniform heat source for controlled heating of a thermal paper sample to a temperature required to develop latent prints.

A further aspect provides apparatus for visualising latent fingerprints deposited onto thermal paper, the apparatus comprising a spatially and temporally uniform heat source.

The apparatus may further comprise an electromagnetic radiation source to improve visualisation of developing prints. The electromagnetic radiation source may emit ultraviolet, visible light or infrared.

The source may emit visible light with a wavelength in the range 390 nm to 750 nm; for example the source may emit light with a peak wavelength of approximately 590 nm, or with a peak wavelength of approximately 395 nm.

The electromagnetic radiation source may comprise one or more emitters. For example the light source may comprise a light-emitting diode (LED). In some embodiments a plurality of emitters are provided in an array. This allows, for example, samples of a variety of sizes to be used with the same array (with more or less of the emitters being redundant accordingly).

The apparatus may comprise a heater and may further comprise a cooler. In some embodiments a combined heating/cooling module is provided, for example a Peltier device.

The heat source may comprise a hot plate or the like.

The apparatus may comprise a substantially flat surface for receiving thermal paper, for example a glass sheet or the like.

The apparatus may comprise a housing which allows illumination and/or observation during heating.

In some embodiments the radiation source is built in to the apparatus, for example into a lid.

The heat source may apply heat from under and/or over the sample and/or laterally.

The apparatus may further comprise a light detector for automatically detecting developing prints. The light detector may comprise a plurality of light detectors in an array. This allows, for example, samples of a variety of sizes to be used with the same array (with more or less of the detectors being redundant and discounted accordingly). In some embodiments the light detector comprises one or more photosites.

In some embodiments the apparatus includes an optical system for detecting prints as they develop; a cooling step may then be activated to prevent overdevelopment.

In some embodiments, for example, the controlled heating of the sample means that pre-existing thermally developed areas, such as text, are still visible after heating.

The apparatus may be provided in the form of a stand-alone system.

The apparatus may comprise an image capture facility. For example, means for capturing an image of the sample may be provided. The image capture may take place before and/or during and/or after a development process. In some embodiments the image capture apparatus may allow for capture of an image of the sample when on/in the apparatus and during heating/lighting. A camera or the like image capture device may, for example, be provided.

Images may be taken during a development process. For example, an image may be taken after heating for a period of time and then further heating may be applied. This allows, for example, further prints to develop whilst preserving the image of others.

The image capture may facilitate a still image. Alternatively or additionally a moving/kinetic image may be captured of the whole or part of a development process.

The image capture apparatus may be linked to a computer or other display device for example for viewing, storage and further processing.

By allowing for a kinetic image of a development process to be viewed remotely but substantially in real time this may allow, for example, for manual control of heating and/or cooling processes if appropriate.

A further aspect provides a method for visualising latent fingerprints deposited onto thermal paper comprising the steps of: providing a heat source; and using the heat source to uniformly heat the thermal paper to develop latent fingerprints.

A further aspect provides a method of heating thermal paper to a temperature required to develop latent friction ridge prints, comprising the steps of: providing a heat source; placing a thermal paper sample onto the heat source; and heating the sample to a development temperature below the normal colour change temperature of the paper whereby to develop latent prints.

A further aspect provides a controlled method of heating thermal paper to a temperature required to develop latent fingerprints, comprising the steps of: providing a heat source; placing a thermal paper sample onto the heat source; and heating the sample to develop latent fingerprints.

The heating step may heat the uniformly heat the sample both spatially and temporally.

The method may further comprise the step of detecting the development of prints. An automatic detection system may be provided to assess the development of prints. The automatic detection may be performed using a light detector; for example by using an array of light detectors.

The method may further comprise the step of illuminating the paper during heating. The paper may, for example, be illuminated with ultraviolet, visible light or infrared. In some embodiments the paper is illuminated with visible light with a wavelength in the range 390 nm to 750 nm; for example approximately 590 nm or approximately 395 nm.

The sample may be illuminated using an array of emitters. In some embodiments the paper is illuminated using one or more light-emitting diodes (LED).

The heat source may heat to a development temperature in the range 30° C. to 150° C., for example in the range 40° C. to 140° C. such as 50° C. to 120° C., 60° C. to 100° C., 70° C. to 80° C., or 45° C. to 47° C. The development temperature and the time heating is applied will be dependent on the individual sample.

Once the prints are sufficiently developed the heating may be stopped. In some embodiments the method then further comprises the step of actively cooling the sample.

A heating step may have duration in the range 10 seconds to 5 minutes. A cooling step may have duration in the range 10 seconds to 5 minutes.

In some embodiments the whole process may take in the region of 1 to 3 minutes.

The method may further comprise the step of further processing the developed sample. For example an image of the developed sample may be taken; and/or the sample may be further analysed as required.

The method may comprise an image capture step. For example, means for capturing an image of the sample may be provided. The image capture step may take place before and/or during and/or after a development process. In some embodiments the method may provide for capture of an image of the sample when on/in the apparatus.

Images may be taken during a development process. For example, an image may be taken after heating for a period of time and then further heating may be applied. This allows, for example, further prints to develop whilst preserving the image of others.

The image capture step may facilitate a still image. Alternatively or additionally a moving/kinetic image may be captured of the whole or part of a development process.

By allowing for a kinetic image of a development process to be viewed remotely but substantially in real time this may allow, for example, for manual control of heating and/or cooling processes if appropriate.

The sample may be substantially static during the process and may remain so throughout.

The method may be substantially non-destructive i.e. the sample is not damaged by the process.

Different aspects and embodiments of the present invention may be used separately or together.

Further particular and preferred aspects of the present invention are set out in the accompanying independent and dependent claims. Features of the dependent claims may be combined with the features of the independent claims as appropriate, and in combination other than those explicitly in the claims.

Figure 1B:
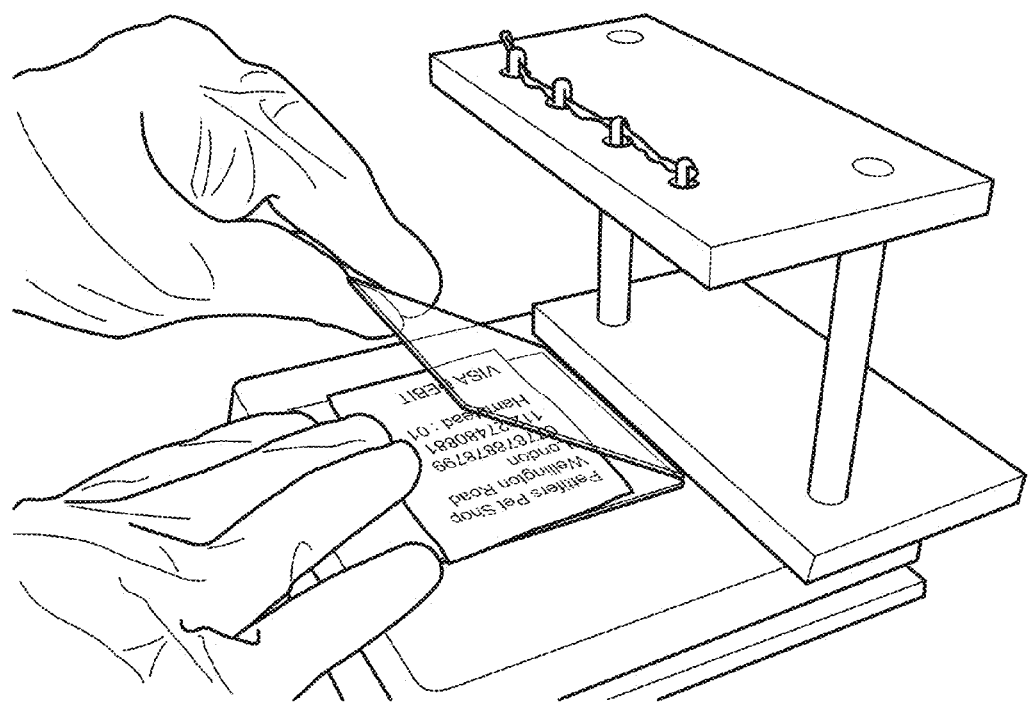
Figure 2:
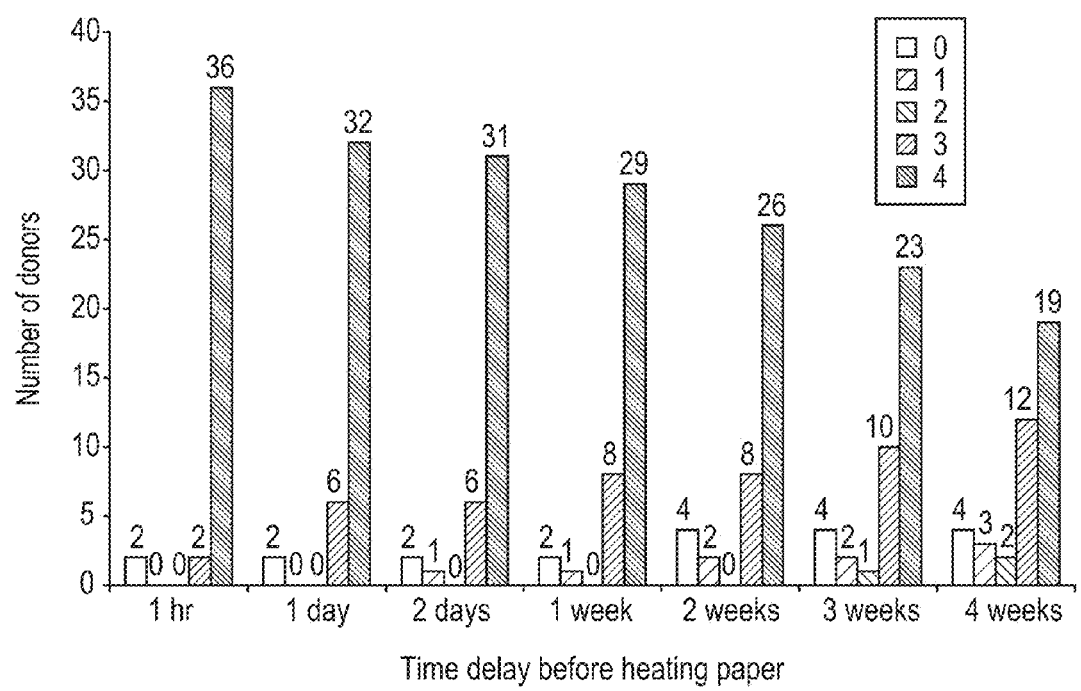
Figure 3:
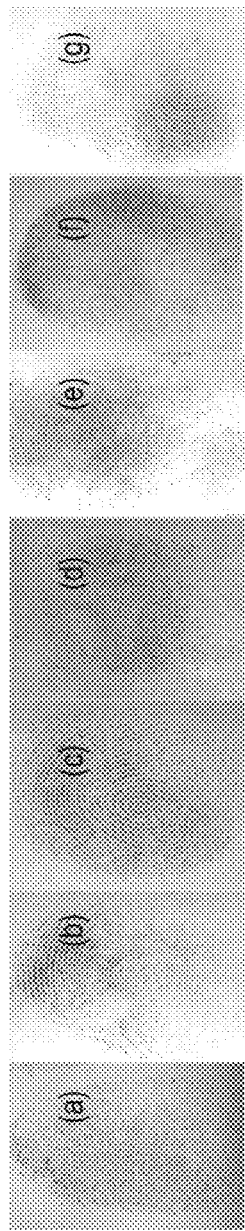
Figure 4:
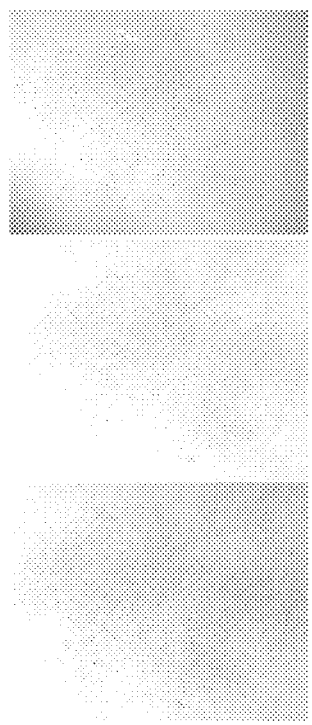
Figure 5:
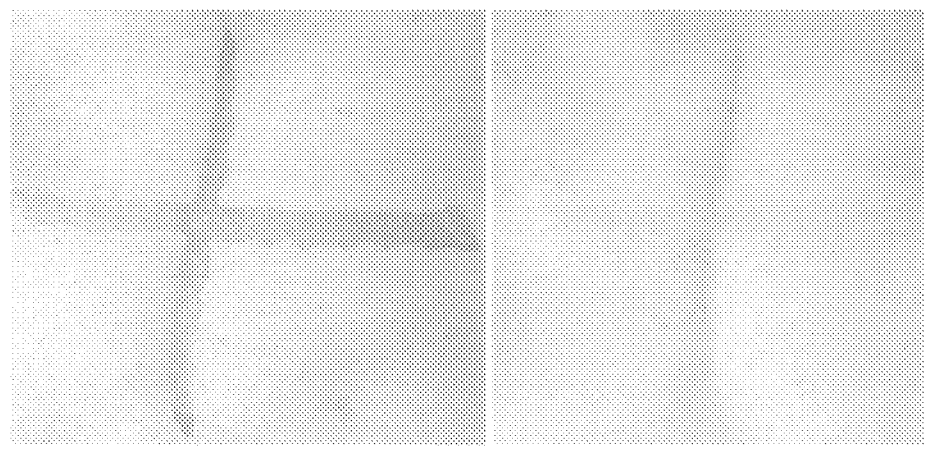
Figure 6:
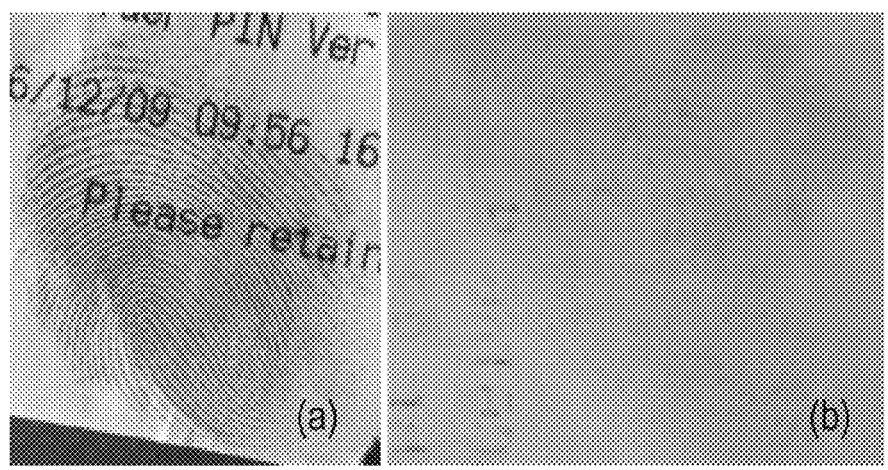
Figure 7:
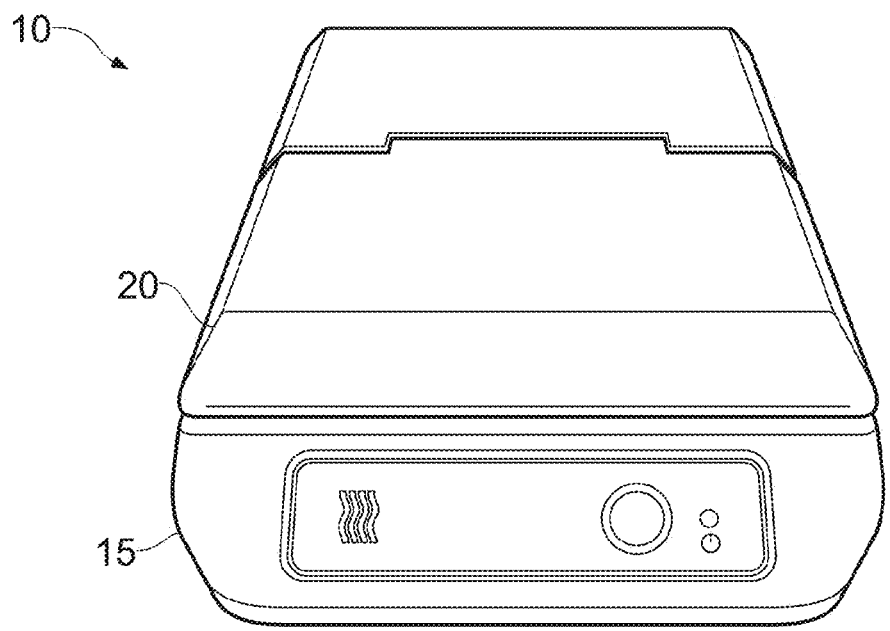
Figure 8:
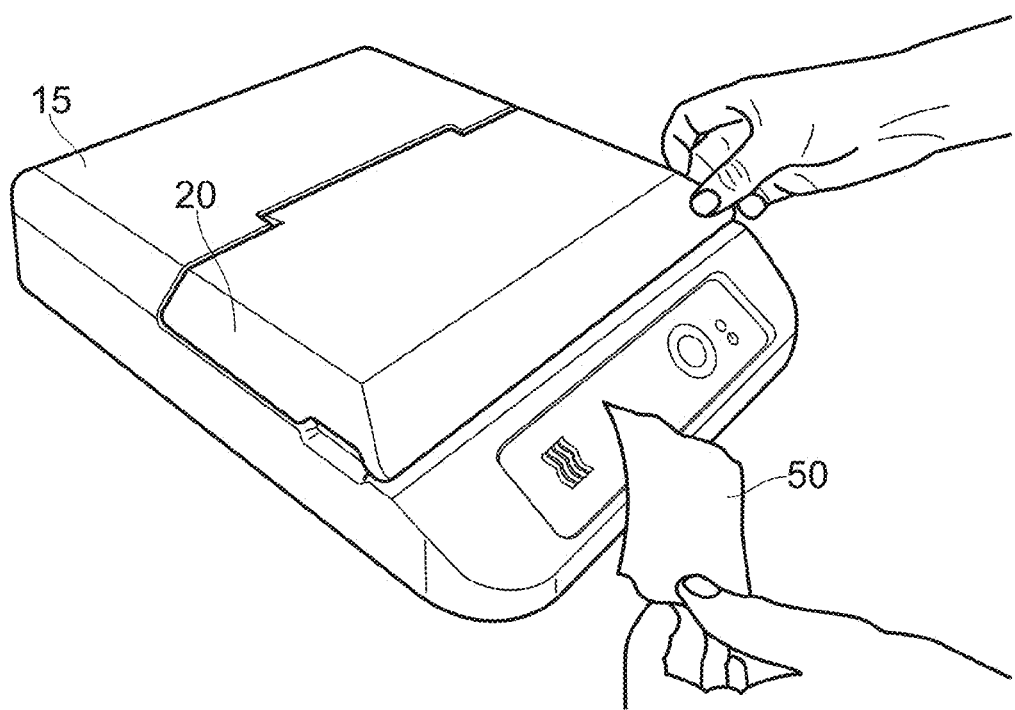
Figure 9:
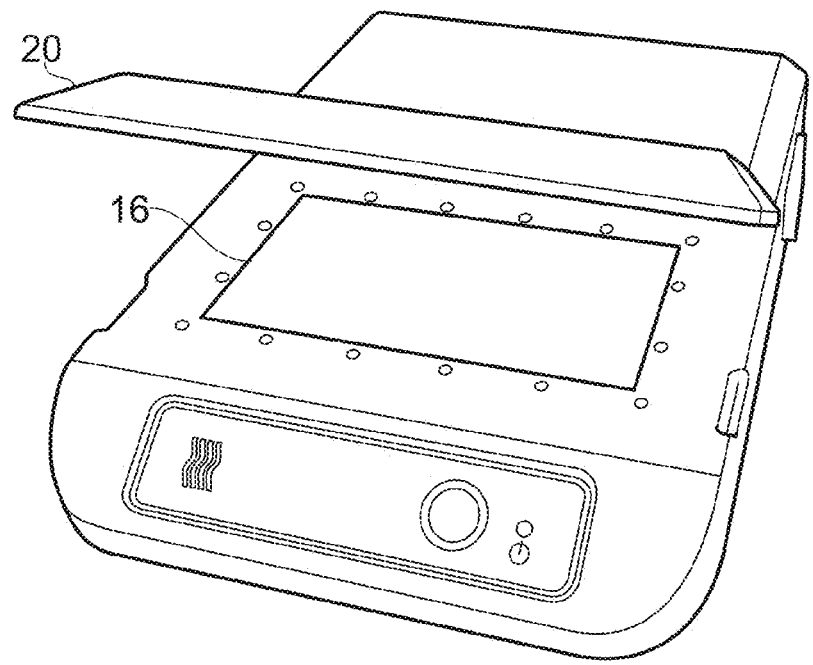
Figure 10:
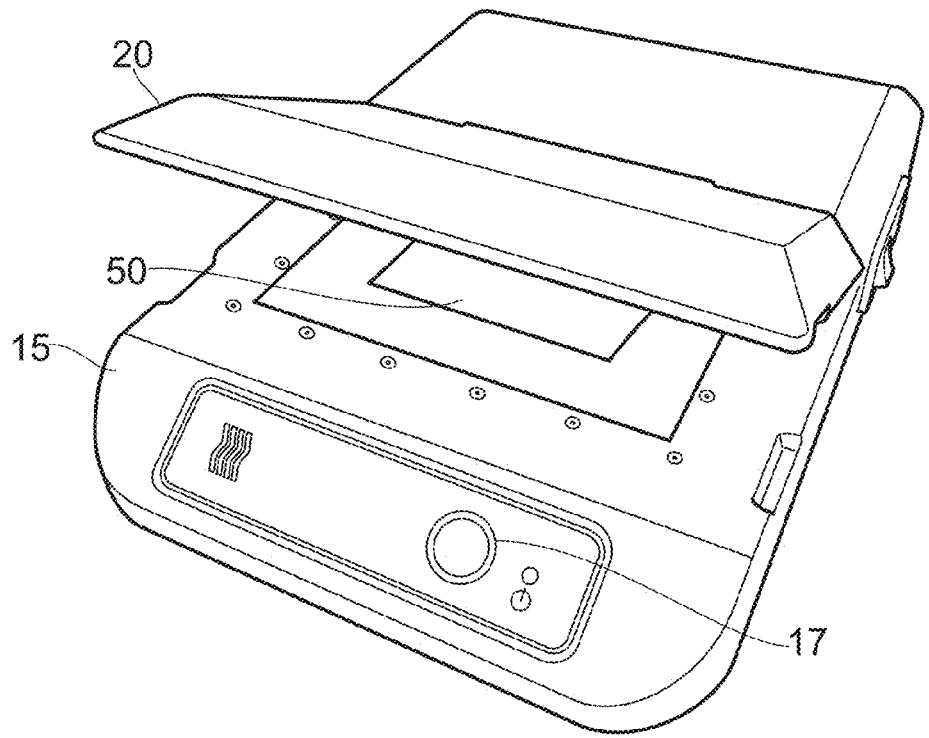
Figure 11:
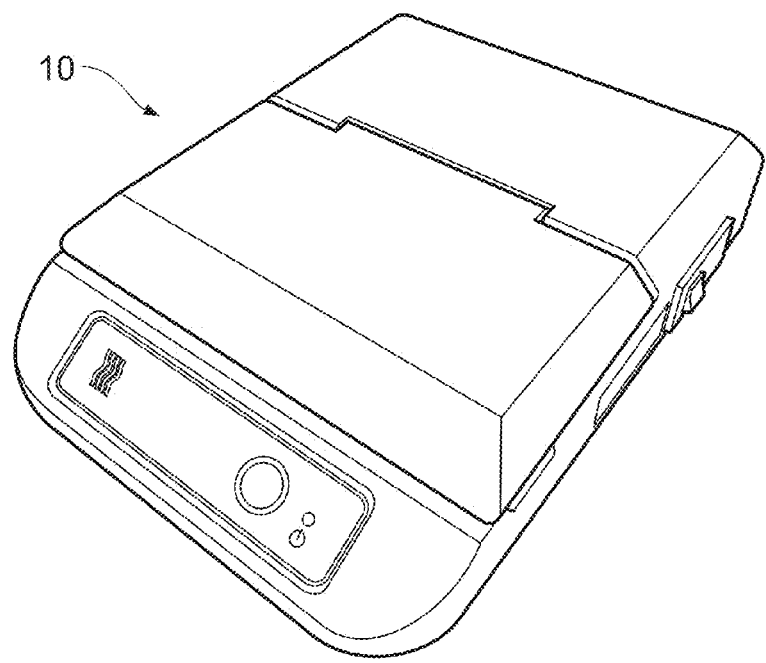
Figure 12:
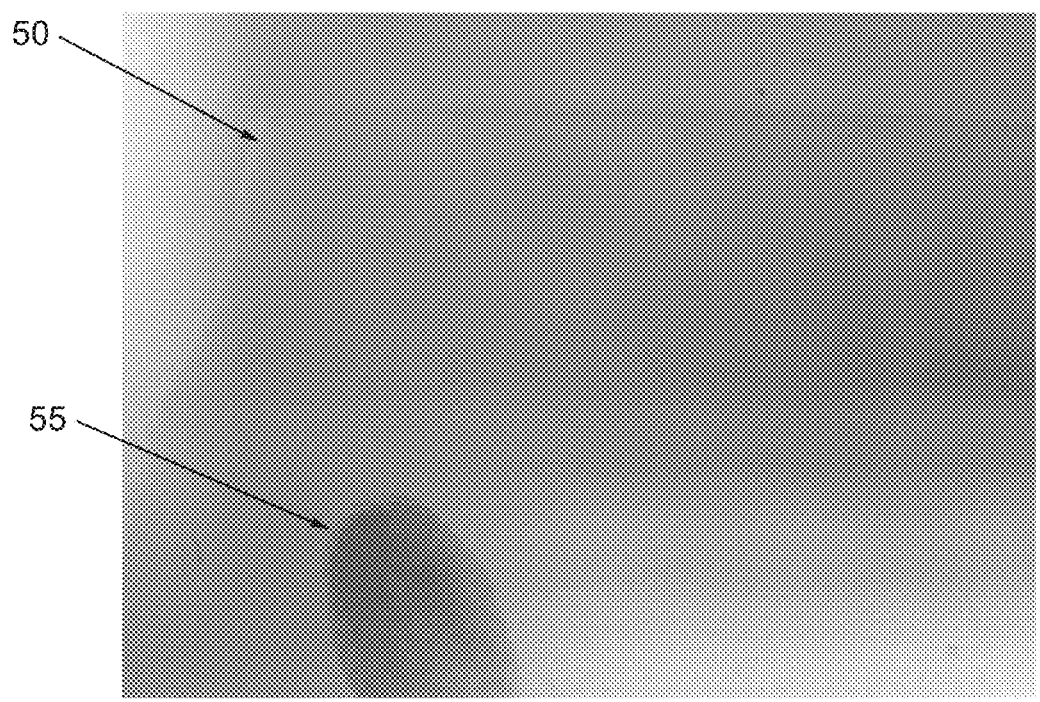
Figure 13:
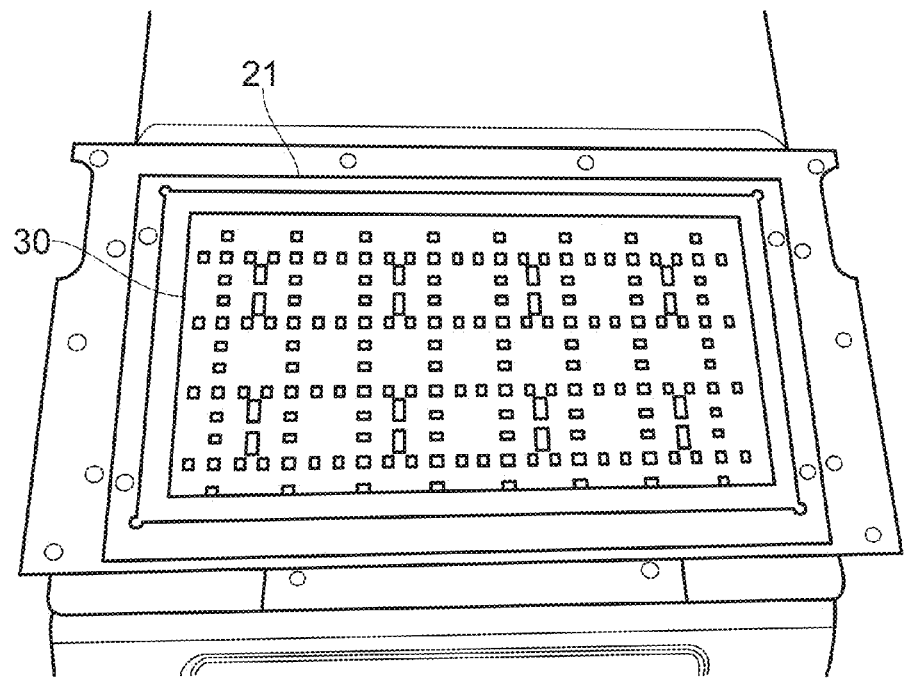
Figure 14:
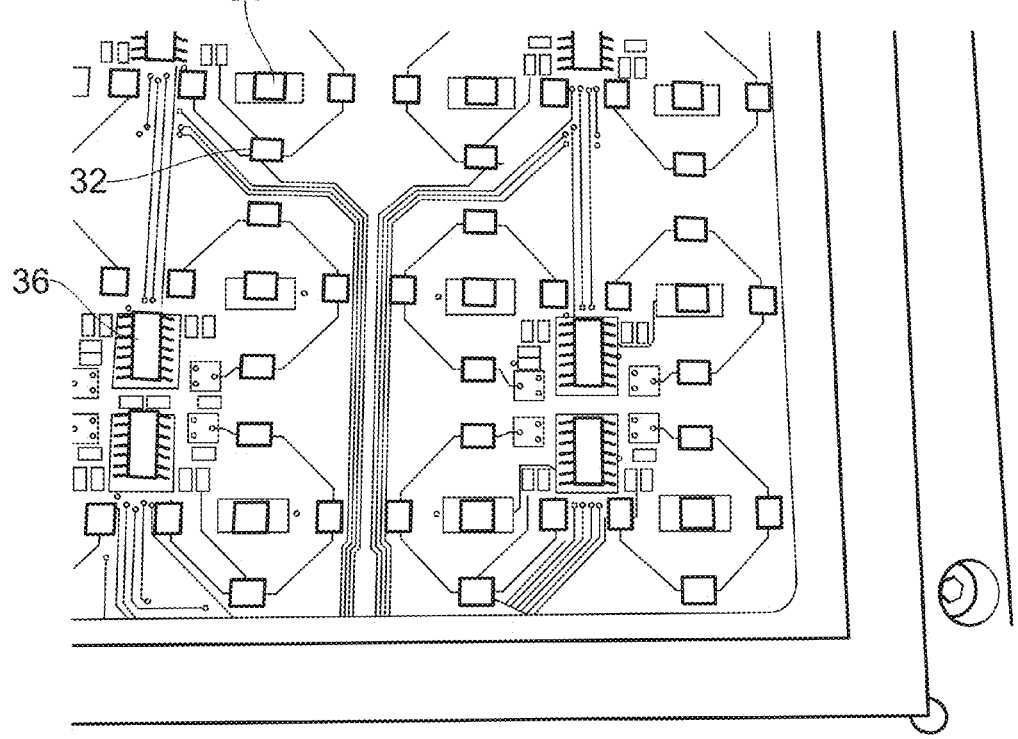
Figure 15:
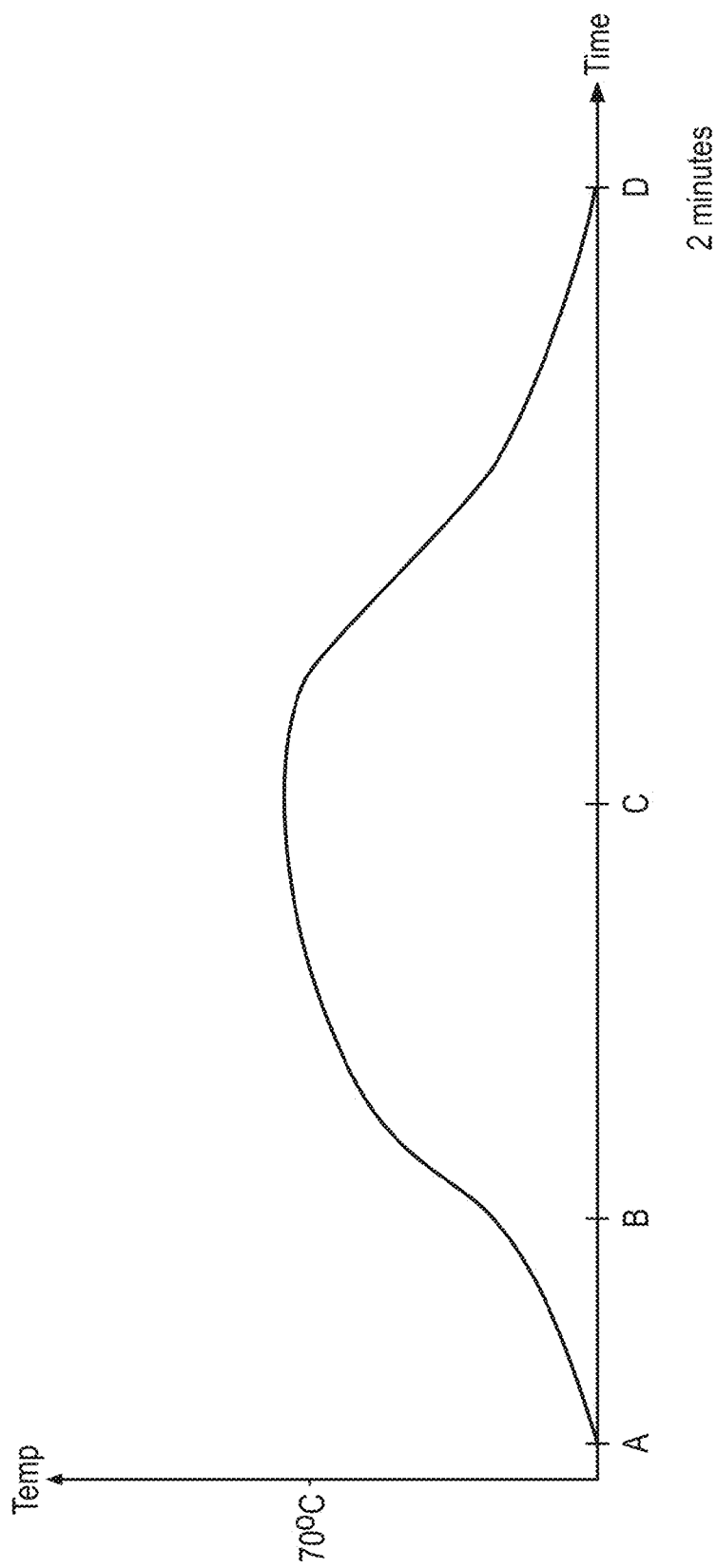

The present invention will now be more particularly described, the way of example, with reference to the accompanying drawings, in which:

FIG. 1(a)—Schematic representation of apparatus used to develop latent fingerprints deposited onto thermal paper;

FIG. 1(b)—Photograph of the apparatus in use;

FIG. 2—Grading of fingerprints developed on thermal paper using the grading scale shown in Table 1;

FIG. 3—Examples of grade 4 developed fingerprints for elapsed times of (a) 1 hr, (b) 1 day, (c) 2 days, (d) 1 week, (e) 2 weeks, (f) 3 weeks and (g) 4 weeks;

FIG. 4—A faint fingerprint developed after 4 weeks elapsed time and photographed with (a) a Daylight™ lamp, (b) a white Crime-Lite and (c) a blue LED;

FIG. 5—A developed mark of (a) lysine solution and (b) distilled water on heated thermal paper;

FIG. 6—Developed fingerprints on (a) a receipt dated 2009 and (b) a receipt dated 2006. Both (a) and (b) were photographed with the blue LED light source;

FIG. 7—a front elevation of a print recovery apparatus formed according to an alternative embodiment;

FIG. 8—a perspective view of the apparatus of FIG. 7 shown with a sample for analysis;

FIG. 9—a perspective view of the apparatus of FIG. 7 and FIG. 8 shown with a lid lifted ready to receive a sample;

FIG. 10—a perspective view of the apparatus of FIG. 9 shown with a sample in position ready for analysis;

FIG. 11—a perspective view of the apparatus of FIG. 10 shown with the lid closed and ready for analysis to commence;

FIG. 12—a photograph of a sample shown following a recovery process in the apparatus of FIGS. 7 to 11;

FIG. 13—a plan view of the underside of the lid of the apparatus of FIGS. 7 to 11;

FIG. 14—a magnified view of a detection cell forming part of a detection array provided by the lid; and FIG. 15—a graph showing an example of a recovery process performed using the apparatus of FIGS. 7 to 11.

An example of apparatus used to heat latent fingerprint deposits on thermal paper is shown schematically in FIG. 1(a) with FIG. 1(b) showing a photograph of the apparatus in use. In FIG. 1(a), A represents a 1 mm thick brass rectangular plate, placed onto the flat surface of a hotplate (Barlowworld Scientific, Stone, UK). To this, via a brass piano hinge (B), is fixed a 1 mm thick glass rectangular plate (C) of similar dimensions to the brass plate such that the glass plate can be raised or lowered. A sample of thermal paper to be treated (D) is placed onto the brass plate and the glass plate lowered to ensure good thermal contact between the paper and brass. E represents a housing for a series of 395 nm peak wavelength LED lamps (F) (Yoldal, Zhonghe City, Taiwan), used to illuminate the thermal paper. Reasons for selection of this illumination wavelength are discussed later.

Latent fingerprint deposits were taken from 20 male and 20 female donors onto thermal paper (Till Rolls Direct, Bletchingly, UK) such that each person donated impressions from seven different fingers. Fingerprints were deposited by pressing a finger onto the paper surface for 1-2 seconds with a light pressure sufficient to ensure contact between the finger and paper. Whilst no attempt was made to regulate the amount of pressure applied by individuals, this procedure was intended to produce reasonably uniform deposition. No artificial stimulation of sweat was employed such as placing the hand in a plastic bag (14) or wearing a latex glove prior to deposition (15). One of the impressions from each donor was developed using the above apparatus after either 1 hr, 1 day, 2 days or 1, 2, 3 or 4 weeks, this time period being in keeping with that considered by Wakefield and Armitage (12). Between deposition and development, the thermal paper was left in an office environment, exposed to both artificial and natural light, but not direct sunlight. Donors had not washed their hands 20 minutes before deposition and, prior to deposition, each donor rubbed their hands together to ensure a uniform distribution of sweat as previous research has indicated that sweat composition can differ between fingers for the same individual (16).

Fingerprint ridge development on thermal paper after the application of heat as described above was graded based on the quality of ridge detail visible (as a black impression on the white paper). For this, the grading system devised by Bandey (17) was used and this is reproduced in Table 1. Initial experimentation determined that, for fingerprint development, the optimum temperature for the top surface of the brass rectangle was 44° C. This was measured across the top surface of the brass rectangle by means of a k-type thermocouple and found to vary both spatially and temporally by $<\pm 0.5°$ C. This development temperature is in keeping with that reported by Wakefield and Armitage (12) of between 45° C. and 47° C. depending on the brand of thermal paper.

Samples from only two of the 40 donors failed to produce any fingerprint ridge development for any of the time periods listed above. Of the remaining 38 donors, FIG. 2 shows that the majority in all time periods gave a grade 4 on the Bandey scale (full ridge development). Over time, the number of donors that gave a grade 4 diminished from 36 (after an elapsed time before heating of 1 hr) to 19 (after an elapsed time of four weeks). However, the number of donors that gave a grading of 0-2 only increased slightly in this time period from two (after 1 hr) to nine (after four weeks). Therefore, the majority of donors (78%) still produced a grading of 3 or 4 after an elapsed time of four weeks. Development time (t) (i.e. the time that the thermal paper was required to be in contact with the brass rectangle for fingerprint development to occur) varied between individual donors in the range $2\ s \leq t \leq 20\ s$. This development time is less than that reported by Wakefield and Armitage (12) and this may be as a result of the improved thermal contact between the heat source used here (the hotplate and brass rectangle) and the thermal paper. There was no evidence to suggest that t increased with elapsed time before development. FIG. 3 shows typical examples of grade 4 development for each of the elapsed times. All images in FIG. 3 were taken whilst the paper was illuminated with a Daylight® lamp (Daylight Company, London U.K.) although office lighting as illumination gave similar results.

The number of developed fingerprints giving grade 3 or 4 after an elapsed time >2 weeks is in contrast to the results of Wakefield and Armitage (12) where no fingerprint development was observed for an elapsed time >2 weeks. As discussed by Wakefield and Armitage, these differences may be due to the variation in chemicals used in the manufacturing process for different brands of thermal paper. Further, Wakefield and Armitage noted that developed fingerprints had faded one week after development. Here, developed fingerprints did not exhibit any fading for at least 26 weeks after development (the time limit of the experiment). Again, this difference may be due to a variation in the chemicals used in the manufacturing process.

It was noticed that, for elapsed times of greater than two weeks, some of the developed images were faint and difficult to see when the paper was under the glass plate and being heated. As this would affect the heating time required (t), a light source to illuminate the paper whilst being heated was investigated. It was found that blue light produced the most visible contrast between the paper and a faint developing fingerprint and so the housing shown as E in FIG. 1 was constructed to enable the paper to be illuminated and observed whilst being heated. FIG. 4 shows a faint fingerprint developed after four weeks elapsed time, and photographed with (a) a Daylight® lamp, (b) a white Crime-Lite (Foster & Freeman, Evesham U.K.) and (c) a blue LED with 395 nm peak wavelength. Whilst having a somewhat 'dotty' appearance, the dots are most distinct when illuminated with the blue LED. It was observed that there was greater transmission of the blue light through the thermal paper compared with both the Daylight® lamp and the white Crime-Lite and this is thought to be contributing to the improved visualization of faint fingerprints.

It was noted above that polar organic solvents initiate colouring of the leuco dye in thermal paper (3). This reaction was investigated further in order to determine the fingerprint sweat components that act as a solvent for the dye and hence are able to reduce the temperature at which it changes colour. Using the same brand of thermal paper as above, various common polar and non-polar solvents were applied to the paper by means of a small brush. The results are shown in Table 2 where it can be seen that, at room temperature and with no additional heating, polar protic solvents (with the exception of water) all increased the solubility of the dye. Thus, for the dye used in this brand of thermal paper, it was assumed that the most favourable solvent would be polar protic, that is, one that can donate a proton attached to (for example) oxygen in a hydroxyl group (OH) or nitrogen in an amino group ($NH_2$) (18).

It is well known that certain amino acids have a polar side chain, including some that are found commonly in eccrine sweat (18). One such amino acid, lysine (16) has an amino group side-chain that is fully protonated in a weak base solution (18).

To test whether a solution of lysine would increase the solubility of the dye, a concentration of 10 $mgL^{-1}$ of lysine was prepared by dissolving the monohydrate (Thermo Fisher Scientific, New Jersey US) in distilled water. This concentration was chosen as it is typical of that found in fingerprint sweat (16). The solution was applied to the thermal paper by means of a small brush. As a control, a similar amount of the distilled water was also applied to the paper. Neither the lysine nor the water gave any colour change to the dye at room temperature. However, on heating using the apparatus described above, a colour change to the dye was noted, which was much more pronounced for lysine than for the water control. The results are shown in FIG. 5 for (a) lysine and (b) water. Thus the amino acid present in eccrine sweat may well be affecting the solubility of the dye observed when heating fingerprint sweat deposits. Fingerprint deposits of eccrine sweat were obtained by asking the same 40 donors to wash their hands in warm soapy water and then to wear a latex glove for 20 minutes before donating fingerprints (14). Results obtained were found to be consistent with those described above.

Samples of used thermal paper, that is, paper that had been used to print receipts etc. were obtained from a variety of sources including automatic teller machines, supermarket checkouts, credit/debit card transactions and supermarket product labels. These samples had been stored since they had been printed and ranged in age from a few days to several years. In total, 50 different receipts were subject to the heat treatment described above. Prints graded 3 or 4 were found on four (8%) of the samples, FIG. 6 showing typical examples from receipts dated 2009 and 2006. In FIG. 6, both developed fingerprints were photographed using the blue LED light source.

By introducing a spatially and temporally uniform heat source, development of fingerprint ridge characteristics deposited as sweat onto thermal paper has been achieved. Results have shown an improvement over previous research, particularly with regard to the visualization of aged or faintly developed fingerprints, by employing a blue LED light source with 395 nm peak wavelength. An investigation of the components in fingerprint sweat that affect the solubility and hence colour change of the dye has shown that polar solvents able to donate a proton are favoured and an amino acid found in eccrine fingerprint sweat (lysine) has been shown to produce the desired colour change. Aged fingerprint deposits on thermal paper from a variety of sources have been visualized with this technique.

Referring now to FIGS. 7 to 15 there is shown a print recovery system for use on thermal paper formed according to an alternative embodiment of the present invention.

The Hot Print System (HPS) general indicated 10 has been designed to recover fingerprint detail from thermal paper. As discussed below the HPS will heat the thermal paper whilst detecting any contrast change in the paper. Once the required contrast change has been achieved, the HPS will rapidly cool the paper, revealing a print.

Referring first to FIGS. 7 to 11 there is shown a print recovery apparatus generally indicated 10. The apparatus 10 comprises a base 15 and a lid 20 hinged to the base. The base 15 comprises a glass sheet 16 forming a flatbed surface for receiving a sample as shown best in FIG. 10). Under the sheet 16 is an array of Peltier devices (not shown) which can selectively heat or cool a sample through the sheet.

Referring now also to FIGS. 13 and 14, the lid 20 carries a frame 21, which in turn carries a printed circuit board which serves as an emission/detection array module 30. The frame 21 is mounted in the lid such that it can move to accommodate variations in the thickness of a sample.

The module 30 includes a plurality of LED's 32 and a plurality of photosites 34 arranged in generally square patterns. A plurality of microprocessor units 36 are also provided and linked to respective sub-arrays of emitters and photo sites.

Referring now also to the graph of FIG. 15, in use, a sample 50 is presented (FIG. 8) and the lid 20 is lifted (FIG.

9) to allow the sample to be laid onto the bed 16 (FIG. 10). In this embodiment the user is instructed to lay the sample with any writing facing upwards as shown. This is stage I on FIG. 15.

Subsequently the lid is closed and a start button 17 on the base is pressed. In a first stage the photosites each take an average reading and discount any that it believes are seeing only the black plate. The system then begins to heat up the sample 50 uniformly.

The photosites read and average the light they receive during the whole heating process. As a result latent prints will start to be developed and this translates into a different level of brightness which can be interpreted as contrast by the photosite array; this is stage II on FIG. 15.

When the value of light received from any one cell reduces beyond a set threshold percentage, scaled to each photosite, this is indicative of the appearance of a print and the heating process will be terminated to prevent further heating of the sample; this is stage III on FIG. 15.

The Peltiers are then be reversed to cool for 30 seconds and then the Peltiers continue to cool for a further 20 seconds. The Peltiers then turn off. The fan continues to work for 90 seconds, after which the process can be repeated (with the same or a different sample). The cooling step therefore protects the sample from overdevelopment; this is stage 1V on FIG. 17.

The sample 50 can now be removed from the device 10 with the developed print 55, as shown in FIG. 12.

There now follows a description of an apparatus forming an embodiment of the present invention. For the avoidance of doubt, all of the following features should be regarded as optional and may be used together or separately.

Power Supply

The internal power supply is an SP320-24 capable of operating from a standard domestic supply of between 90 v and 264V AC, 47-63 Hz.

The internal power supply is capable of operating from a 12 v vehicle supply.

The maximum power consumption is approximately 30 W.

The unit is inherently safe.

It is not be possible for the user to come into contact inadvertently with any electrical or mechanical elements inside.

The HPS has an automatic shutdown should a defined time out be exceeded.

There is a power switch, which will immediately cut all power to the unit.

The unit has a safety warning sticker on it.

When supplied to a user, the unit has a band around the packages which instructs the customer to read the instruction manual before use.

The unit has a 250V 2 AMP fuse incorporated in to the IEC socket

Internal Mechanism

The product is cooled by two 12 v fans.

The product has four different IEC connector plugs for the four different likely sockets (UK, Europe, US and Australasia).

The product has a power lead capable of operating from a 12 v vehicle supply.

The product has an internal power supply to allow main connection from 110-240 v.

The heat source is eight Peltiers.

The Peltiers are mounted between two plates; the top plate is 0.5 mm aluminium and the bottom plate is a 3 mm aluminium heat sink.

The Peltiers are adhered to the plates with thermally conductive double sided tape.

The top plate is anodised.

The bottom heat sink is anodised.

The Peltier wiring comes out of the side of the Peltier heat plate.

The heat plate is mounted to the underside of the main housing.

The product has a door open switch comprising of a reed switch and a magnet.

The cover supports the door open switch.

The lid supports the magnet.

The product has a 24V internal power supply.

The power supply is mounted upside down using four brackets.

The main PCB is mounted on top of the upside down power supply with 3 mm spacers.

The Mosfet power transistors from the main board are mounted to a heat sink which in turn will be mounted to the power supply.

The product has a photosite board to detect the contrast change in thermal paper when heated.

Clips are used to hold the fan wires in place.

The PVC glass holder is sprung inside the lid.

The lid has four inserts to hold the PVC glass holder.

The photosite PCB is attached to the PVC glass holder.

The photosite PCB shall not be warped or twisted.

The glass is flat and 2 mm thick.

The glass is bonded to a stainless steel frame using a jig and double-sided adhesive.

The stainless steel frame is bonded to a PVC holder using a double sided adhesive.

There are two brass blocks inside the lid to add extra weight.

Housing

Base Plate

The product will have an aluminium base plate which is 1.6 mm thick.

Fan holes match the power supply.

The base plate has two angled fan holes.

The fans have finger guard as an integral part of the base.

Foam fin air deflectors will be used around the fans.

The base plate is mounted on five rubber feet.

The base plate has a Grain Finish (240 Grit).

Main Housing

The main housing is of solid construction.

The main housing is polycarbonate which is screwed on to the base plate.

The main housing has a partition between the Peltier heated section and the power supply section. This has a single hole drilled to route the Peltier wiring and a slot to route the fan wires, door switch wire and ribbon cables.

The main housing has a second partition between the Peltier heated section and the front panel section which will have a cut out to house the ribbon cables.

The main housing has M4 inserts moulded in.

The main housing cover houses a reed switch.

The main housing houses an IEC socket to the right rear.

The wiring is routed in a tidy manner to the right rear of the main housing when viewed from the top.

Lid

The product has a plastic polycarbonate lid which will be hinged to the cover.

The lid has a PVC glass holder.

The PVC glass holder houses a stainless steel frame.

The stainless steel frame houses 2 mm thick glass.

The lid has M3 inserts moulded in to fix the inner frame and M2.5 inserts moulded in to fix the PVC glass holder in place.

The lid has a black anodised aluminium frame to hold the PVC frame.

The lid houses a magnet for the door switch.

Front Panel

The front panel PCB is mounted to the main housing.

The main housing has 2 mm spacers to mount the front panel PCB.

The main housing supports the front panel graphic.

The front panel graphic is mounted with double sided adhesive to the cover.

The front panel graphic sandwiches the acrylic light guide to the cover.

The front panel graphic sandwiches the switch piston to the cover.

Electronics

Power Supply

The product has a 24 v internal power supply.

The power supply connects to mains power from 110-240 v.

The power supply connects to mains power using an IEC lead into an IEC connector.

The IEC connector is fitted with 250 v 2 AMP 20 mm fuses.

The power supply is earthed to the base plate.

The unit is able to facilitate an IEC filter if needed and will use flag terminals in that case.

If no filter is used, standard ¼" blade terminals can be used.

The IEC is connected to the power supply with 1 off 200 mm lengths each of wire, brown, blue and yellow/green.

The power supply connects from the positive and negative terminals to PL10 on the main PCB using 2 red/black figure of eight cables 250 mm in length.

Main Printed Circuit Board (PCB)

The main PCB is mounted on top of the upside down power supply with 3 mm spacers.

The Mosfet powers transistors from the main PCB are mounted to a heat sink which is mounted to the power supply.

Photosite PCB

The photosite PCB detects the contrast change in thermal paper when heated.

The photosite PCB has yellow LEDs.

The photosite PCB has photodiodes.

The photosite PCB has a separate cell which scales the photodiodes individually for factory calibration.

The photosite PCB is mounted to the PVC glass holder 16 mm away from the glass.

The photosite PCB will not be warped or twisted.

The photosite PCB has a black solder resist.

The photosite PCB is connected to SK2 on the main PCB using a 200 mm flat flex cable routed through the lid.

Front Panel PCB

The product has a front panel with a single operation icon, push button and power light to show the status, as per the following:

Power Icon:
   Green for on
   Red for error

Heating Icon:
   Green for ready
   Amber flashing for when machine in process (Peltier heat and cool)
   Amber steady for when pettier cooling process is complete along with a two beeps
   Green when the system has cooled
   Red flashing if there is a problem Push Button:
   White and constantly on (even during standby)
   There will be 1 long error beep if the cycle has timed out.

The front panel is powered by the main PCB.

The front panel is connected to PL2 on the main PCB using a 500 mm ribbon cable

The front panel ribbon cable is routed from the front panel round to the right rear as viewed from the top and through both partitions Peltiers There are eight peltiers in series in two strings of four.

The Peltiers are linked by closed end crimps.

The Peltier plate connects to PL8 on the main PCB using 2 red/black figure of eight cables.

Fans

The product is cooled by two 12 v fans.

The fans are connected to PL5 and PL6 on the main PCB.

Door Switch

The door switch will be a reed switch and magnet.

The door switch will be connected to PL1 on the main PCB.

Software/Firmware

Factory Calibration

1. The system will have a known white material placed under all photosites.
2. The photosites will be turned on and the LED current increased until the photosite with the highest averaged reading approaches the maximum signal (30,xxx).
3. The average reading will be the average of approximately sixteen readings, but more or less as required to achieve stable measurements.
4. At this point the system will record the average readings from each of the photosites and the PWM value for the LED drive current. This will be the level used for normal operation.
5. Each photosite reading recorded at the calibration will be used to scale subsequent photosite readings.
6. The white sheet will be removed to allow a view of the black plate.
7. The photosites will then look at the plate under the known illumination and capture each photosites average reading of the black plate.
8. This is now calibrated as the machine knows what white and black looks like.

User Process

1. The user inserts the sample and presses the button.
2. The fans will start at hex value 0xFF and will operate any time the Peltiers are working.
3. The photosites each take an average reading and discount any that it believes are seeing only the black plate.
4. The system will heat at hex value 0xB5 until the photosites sense a change.
5. The photosites will continue to be read and averaged during the whole heating process.
6. When the value from any one cell reduces beyond a set threshold percentage, scaled to each photosite (to be specified through testing), the heating process will be terminated.
7. The Peltier will then be reversed at hex value 0xFF to cool for 30 seconds.
8. After 30 seconds the Peltier will continue to cool at hex value 0x29 for 20 seconds.
9. The Peltiers will now turn off.

10. The fan will continue to work for 90 seconds.
11. After 90 seconds the process can be repeated.

Functionality

The HPS has the following functions:
1. The machine is plugged in to the mains and the power switch light is off.
2. The power button is turned on, the power switch illuminates and the machine goes to its ready state illuminating the green power light, button light and green icon lights on the front panel.
3. The user will lift the lid, insert the paper, lower the lid and press the button to start the process.
4. The icon light will turn flashing amber to show it is in progress.
5. The system will heat and sense IAW firmware.
6. Once the system has sensed the change, there will be a single audible signal and the heating icon will show steady amber. The user will then open the door to remove the sample.
7. Once the system has cooled to a safe temperature (IAW firmware) the icon will turn green (back to function 4).
8. If there is a critical error in the process the icon flashes red.
9. If the button is pressed with the door open there will be an error sound and process won't start.
10. Instructions The customer needs to be guided to:

Only process thermal paper

Put the paper in writing side up

Only put thermal paper in the machine (no thick objects)

Use only plastic tweezers

Understand that the unit is hot

Not lift the lid during processing

Understand to only push the button in standby state or when the icon is green

Only place the system on an flat well ventilated surface

A defined cleaning regime

Calibration

The unit self-calibrates every time it is powered.

The customer will have a means of reliably testing the calibration of the machine.

Portability

The HPS is intended to be primarily used on a laboratory bench.

The HPS can also be used in a vehicle.

The HPS may have a reusable carry case to allow safe transport, for example when calibration/repair is due.

Although illustrative embodiments of the invention have been disclosed in detail herein, with reference to the accompanying drawings, it is understood that the invention is not limited to the precise embodiments shown and that various changes and modifications can be effected therein by one skilled in the art without departing from the scope of the invention as defined by the appended claims and their equivalents.

REFERENCES 1. http://ezinearticles.com/?The-Uses-and-Hazards-of-Thermal-Paper&id=4141727
2. Bowman V, editor. Manual of fingerprint development techniques. $2^{nd}$ rev. ed. Sandridge, UK: Police Scientific Development Branch, Home Office, 2004.
3. http://www.bvda.com/EN/prdctinf/en_thermanin.html.
4. Broniek B, Knaap W. Latent fingerprint development on thermal paper using muriatic (hydrochloric) acid. J Forensic Ident 2002; 52:427-32.
5. Schwarz L, Frerichs I. Advanced solvent-free application of ninhydrin for detection of latent fingerprints on thermal paper and other surfaces. J Forensic Sci 2002; 47:1274-7.
6. Sears V. Latent fingerprint development on thermal paper using muriatic (hydrochloric) acid. J Forensic Ident 2002; 52:678.
7. Ma R. Chemical fuming: a practical method for fingerprint development on thermal paper. J Forensic Ident 2006; 56:364-73.
8. Takatsu M, Kageyama H, Hirata K, Akashi S, Yoko Ta T et al. Development of a new method to detect latent fingerprints on thermal paper with o-alkyl derivative of ninhydrin. Rep Nat Res Inst Police Sci 1991; 44:1-6.
9. Schwarz L, Klenke I. Enhancement of ninhydrin or DFO treated latent fingerprints on thermal paper. J Forensic Sci 2007; 52:649-55.
10. Schwarz L, Klenke I. Improvement in latent fingerprint detection on thermal paper using a one-step ninhydrin treatment with polyvinylpyrrolidones (PVP). J Forensic Sci 2010; 55:1076-9.
11. http://www.clpex.com/Articles/TheDetail/1-99/TheDetail97.htm.
12. Wakefield M, Armitage S. The development of latent fingerprints on thermal paper using a novel, solvent-free method. J Forensic Ident 2005; 55:202-13.
13. Scott M. Improved results in the development of latent fingerprints on thermal paper. J Forensic Ident 2008; 58:424-8.
14. Migron Y, Hocherman G, Springer E, Almog J, Mandler D. Visualization of sebaceous fingerprints on fired cartridge cases: A laboratory study. J Forensic Sci 1998; 43:543-548.
15. Worley C G, Wiltshire S S, Miller T C, Havrilla G J, Majidi V. Detection of visible and latent fingerprints using micro-x-ray fluorescence elemental imaging. J Forensic Sci 2006; 51:57-63.
16. Ramotowski R S. Composition of latent finger print residue. In: Lee H C, Gaensslen R E, editors. Advances in fingerprint technology. New York: Elsevier, 2001; 63-104.
17. Bandey H L. Fingerprint development and imaging newsletter: The powders process, study 1. Sandridge: Police Scientific Development Branch, Home Office; 2004 Report No.:54/04.
18. Clayden J, Greeves N, Warren S, Wothers P. Organic Chemistry. Oxford: Oxford University Press; 2001.

TABLE 1

Grading system for determining the quality of ridge detail for enhanced fingerprints devised by Bandey (17).

| Grade | Comments |
| --- | --- |
| 0 | No development |
| 1 | No continuous ridges. All discontinuous or dotty. |
| 2 | One third of mark continuous ridges. (Rest no development, dotty). |
| 3 | Two thirds of mark continuous ridges. (Rest no development, dotty). |
| 4 | Full development. Whole mark continuous ridges. |

TABLE 2

Effect of various solvents on the solubility of the dye in thermal paper at room temperature.

| Solvent | Paper changed colour? | Solvent category |
| --- | --- | --- |
| Acetic acid | Yes | Polar protic |
| Dichloromethane | No | Polar aprotic |

TABLE 2-continued

Effect of various solvents on the solubility of
the dye in thermal paper at room temperature.

| Solvent | Paper changed colour? | Solvent category |
|---|---|---|
| Ethanol | Yes | Polar protic |
| Ethyl acetate | No | Polar aprotic |
| Isopropyl alcohol | Yes | Polar protic |
| Methanol | Yes | Polar protic |
| Toluene | No | Non-polar |
| Water | No | Polar protic |

The invention claimed is:

1. A method for developing a latent fingerprint deposited onto the surface of a portion thermal paper, the method comprising the steps of:

commencing uniform heating of the portion of thermal paper to raise the temperature thereof to a temperature which is below the normal temperature at which the surface layer changes color;

monitoring the contrast of a developing fingerprint; and terminating heating when the contrast of the developing fingerprint reaches a desired state or decreases by a pre-determined threshold percentage.

2. A method as claimed in claim 1, in which the step of monitoring the contrast of a developing fingerprint is performed using an array of light detectors.

3. A method as claimed in claim 1, in which the portion of thermal paper is actively cooled after heating is terminated.

4. A method as claimed in claim 1 in which the surface layer of the portion of thermal paper is illuminated during heating.

5. A method as claimed in claim 4, in which the paper is illuminated with ultraviolet, visible light or infrared.

* * * * *